US006240960B1

(12) United States Patent
Fillmore

(10) Patent No.: US 6,240,960 B1
(45) Date of Patent: Jun. 5, 2001

(54) BACK FLUSH VALVE FOR ONE-WAY FLUSH OF DRAINAGE CATHETERS

(76) Inventor: David J. Fillmore, 3062 E. 38th Pl., Tulsa, OK (US) 74105

(*) Notice: Subject to any disclaimer, the term of this patent is extended or adjusted under 35 U.S.C. 154(b) by 0 days.

(21) Appl. No.: 09/257,612

(22) Filed: Feb. 25, 1999

Related U.S. Application Data

(60) Provisional application No. 60/076,093, filed on Feb. 26, 1998.

(51) Int. Cl.[7] .............................. F16K 11/07; F16K 11/14
(52) U.S. Cl. ....................................... 137/607; 137/625.4
(58) Field of Search ............................... 137/607, 625.4, 137/597; 604/33, 34, 258

(56) References Cited

U.S. PATENT DOCUMENTS

| 754,760 | * | 3/1904 | Fesenfeld | 251/149.3 |
|---|---|---|---|---|
| 2,474,286 | | 6/1949 | Snyder | 137/111 |
| 3,416,567 | | 12/1968 | Von Dardel et al. | 137/604 |
| 3,699,964 | | 10/1972 | Ericson | 128/275 |
| 3,906,935 | | 9/1975 | Raia et al. | 128/2 F |
| 4,765,367 | | 8/1988 | Scott | 137/607 |
| 5,030,210 | | 7/1991 | Alchas | 604/247 |
| 5,083,561 | | 1/1992 | Russo | 128/207.16 |
| 5,220,916 | | 6/1993 | Russo | 128/207.16 |
| 5,346,470 | | 9/1994 | Hobbs et al. | 604/24 |
| 5,360,412 | | 11/1994 | Nakao et al. | 604/247 |
| 5,549,651 | * | 8/1996 | Lynn | 604/283 |
| 5,645,538 | | 7/1997 | Richmond | 604/256 |
| 5,676,136 | | 10/1997 | Russo | 128/205.24 |
| 5,730,727 | | 3/1998 | Russo | 604/118 |
| 5,775,325 | | 7/1998 | Russo | 128/205.12 |

\* cited by examiner

Primary Examiner—Stephen M. Hepperle
(74) Attorney, Agent, or Firm—Workman, Nydegger & Seeley

(57) ABSTRACT

A valve apparatus is provided that comprises a housing with a passageway formed therethrough and a seal assembly. The housing has an access port with a bore formed therein that is configured to be in fluid communication with the passageway. The seal assembly is configured to automatically seal and unseal the passageway in the housing in response to a medical device being attached to the access port. The seal assembly has an open position where the passageway of the housing is capable of having fluid flow therethrough and a closed position in which the fluid flow through the passageway is interrupted. The seal assembly is configured to automatically move between the open position and the closed position. The seal assembly is biased into the normally open position. The seal assembly also has a hole formed therethrough which communicates with the bore in the access port and provides an opening to the passageway of the housing when the seal assembly is in the closed position. The seal assembly comprises a seal and a biasing mechanism. The seal is sized and configured to be movably disposed in the bore of the access port. The seal has a substantially cylindrical shape. The biasing mechanism comprises a resilient flexible member configured to cooperate with the seal so as to urge the seal into the open position. The seal and the resilient flexible member are configured to cooperate so as to urge the seal into the open position.

25 Claims, 5 Drawing Sheets

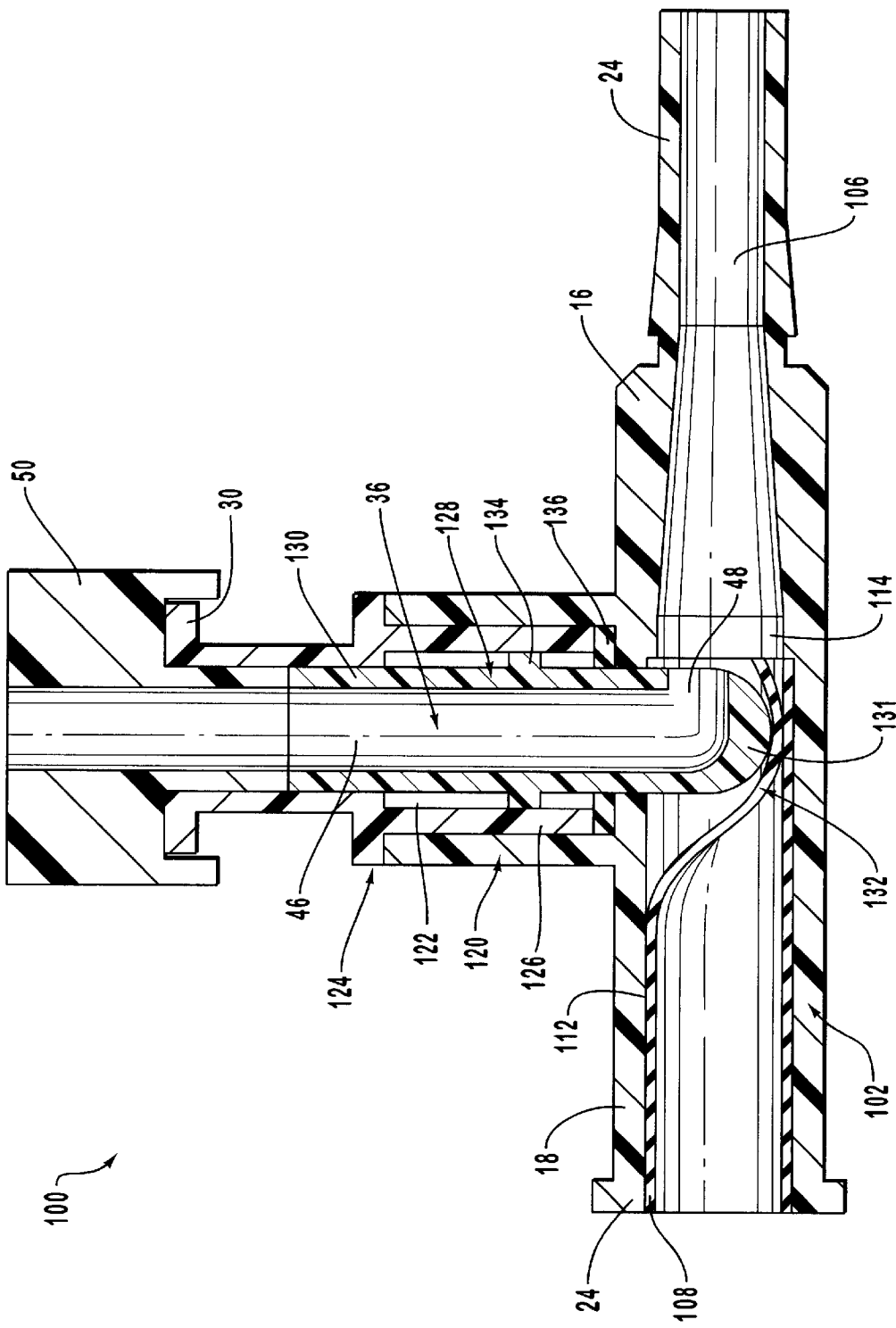

BACK FLUSH VALVE FOR ONE-WAY FLUSH OF DRAINAGE CATHETERS

Related Applications

The benefit of the earlier filing date of U.S. Provisional Patent Application Ser. No. 60/076,093, filed on Feb. 26, 1998, is claimed for this application under 35 U.S.C. § 119(e).

BACKGROUND OF THE INVENTION

1. Field of Invention

The present invention relates to valves, and, in particular, to valves used in flushing procedures for catheters or tubes.

2. Relevant Technology

In the medical field, tubes and catheters are used in a wide variety of applications including drainage procedures or applications. In these type of applications, the tubes or catheters are of the type which carry various bodily fluids, including but not limited to, abscess fluids, urinary fluids, or biliary fluids. One purpose of these tubes or catheters is to decompress, relieve, or drain a specific collection of fluid. The expressed fluid is amassed into a collection bag for evaluation or evacuation.

It is important that the interior passageway or lumen in these devices remain unobstructed from such things as particulates and/or residues which may collect or build-up on the surface of the lumen in the catheter or tube. The buildup of particulates and/or residues on the interior surface of the lumen in the tube or catheter may lead to uneven, reduced, or obstructed flow. Obstructed, limited, or even uneven fluid flow may extend the recovery time of a patient, resulting in the potential for further complications or infections. For example, an infection may cause complications in the patient's treatment leading to sickness or even death. These problems are particularly accentuated with those catheters or tubes which are kept in place for longer periods of time.

As a result, the tubes or catheters must be periodically flushed to ensure that there is not a build-up of particulates or residue in the lumen that will block or impede the flow of fluid out of the patient. Flushing these medical devices usually involves attaching a source of cleansing fluid, such as a saline solution, and directing the cleansing fluid under low pressure through the tube or catheter to remove any buildup occurring in the lumen. The fluid is then allowed to flow out the tube or catheter into the drainage bag.

When it is time to flush the tube or catheter, the drainage bag must be disconnected and the source of cleansing fluid, usually a syringe, is attached to the tube or catheter that is fluidly connected to the patient. Once the cleansing fluid has been directed into the tube or catheter, the syringe or other source of cleansing fluid, must be disconnected and the drainage bag is reattached. This procedure is particularly unsatisfactory because of the time required to unscrew the drainage bag, attach the syringe, and then to unscrew the syringe and reattach the drainage bag. In addition, after the cleansing fluid has been directed into the tube or catheter that is attached to the patient, there is particularly a risk of fluid leaking during the unattaching and reattaching process which can cause an unsanitary condition and potentially expose medical personnel and the patient to contamination. Further, if any fluid is accidentally discharged during this process, the medical personnel must take the time to sanitize the patient, the bedding, and themselves.

Another device, commonly referred to as a stopcock, can be used to make the flushing procedure somewhat easier for medical personnel and to reduce the risk of contamination and spillage. The stopcock is attached to the tube or catheter that is fluidly connected to the patient and connects the tube or catheter to the drainage bag. Typically the stopcock has a valve that must be manually moved by the medical personnel who is going to perform the flushing procedure to direct the flow of fluid either into a drainage bag or to an outside port for periodic catheter maintenance or flushing. This allows the fluid source, such as a syringe, to be attached to the outside port when it is time to flush the tube or catheter. One the syringe is attached, the stopcock is manually moved to stop the fluid flowing to the drainage bag. This allows the cleansing fluid to be directed into the tube or catheter. Once all the cleaning fluid is in the tube or catheter, the stopcock is manually moved back to its original position allowing fluid to flow into the drainage bag.

While the stopcock is an improvement over the manual flushing procedure, there have been various problems with the stopcock. Stopcocks have failed from usage or have had certain limitations to their use. One of the problems with using a stopcock is that the nurse or attendant must manually adjust the stopcock to cease the flow of fluid in the drainage catheter and open the access port to enable the flushing fluid to be directed into the lumen of the tube or catheter. Once the cleansing fluid has been directed into the tube or the catheter, the stopcock must again be manually adjusted to redirect the fluid flow into the drainage bag. These extra steps are time consuming and cumbersome, often wasting the attendant's and/or nurse's time which is valuable and often in short supply. There is also a possibility that the manual adjustments that are required may confuse the medical personnel which then has the potential to misdirect the fluid flow out of the patient. In addition, if for some reason the medical personnel fails to return the stopcock to the original position which allows the fluid to flow to the drainage bag, fluid will flow out the access port and contaminate the patient and generally create a mess. This could result in loss of fluids that are needed to monitor the health of the patient as well as creating an unsanitary condition. A further problem with existing stopcocks is that the diameter of the passageway formed through the stopcock is typically smaller the diameter of the lumen in the tube or catheter that the stopcock is attached to. As a result, the passageway of the stopcock impedes the fluid flow by creating a bottlenecking-effect as the fluid tries to flow through the stopcock.

SUMMARY AND OBJECTS OF THE INVENTION

It is an object of the present invention to provide a valve apparatus that automatically moves from an open position allowing a tube or catheter to drain fluids to a closed position in which the tube or catheter can be flushed but will not accidentally release fluids.

It is yet another object of the present invention to provide a valve apparatus that automatically seals and unseals the passageway in the apparatus in response to attaching an additional line or syringe to the access port, thereby removing any potential for confusion and/or misdirection of the fluid flow.

It is yet another object of the present invention to provide a valve apparatus that automatically moves between an open position in which the passageway in the apparatus is capable of having fluid flow therethrough and a closed position in which the fluid flow through a passageway is interrupted.

Another object of the present invention is to provide for an automatic valve apparatus that reduces the time and inconvenience of the flushing process for medical personnel, and thus reducing the medical costs associated with maintenance of catheters and tubes.

A further object of the present invention is to provide a valve apparatus that does not adversely effect the fluid flowing through the tube or catheter and eliminates the bottleneckeffect created by conventional stopcocks.

These and other objects and features of the present invention will become more fully apparent in the following description and appended claim, or may be learned by the practice of the invention as is set forth herein.

To achieve the foregoing objects, in accordance with the invention as embodied and broadly described herein a valve apparatus is provided that comprises a housing with a passageway formed therethrough and a seal assembly. The housing has an access port with a bore formed therein that is configured to be in fluid communication with the passageway. The seal assembly is configured to automatically seal and unseal the passageway in the housing in response to a medical device being attached to the access port. The seal assembly has an open position where the passageway of the housing is capable of having fluid flow therethrough and a closed position in which the fluid flow through the passageway is interrupted. The seal assembly is configured to automatically move between the open position and the closed position. The seal assembly is biased into the normally open position.

The seal assembly also has a hole formed therethrough which communicates with the bore in the access port and provides an opening to the passageway of the housing when the seal assembly is in the closed position. The seal assembly comprises a seal and a biasing mechanism. The seal is sized and configured to be movably disposed in the bore of the access port. In one embodiment, the seal has a substantially cylindrical shape. The biasing mechanism comprises a resilient flexible member configured to cooperate with the seal so as to urge the seal into the open position.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 5 is an enlarged cross-sectional view of the structure of FIG. 4 with the seal assembly in the closed position.

DETAILED DESCRIPTION OF THE PREFERRED EMBODIMENTS

The present invention is a valve apparatus that automatically moves from an open position allowing fluid to flow out of a tube or catheter through a passageway in the valve apparatus to a closed position in which the fluid flow through the passageway in the valve apparatus is interrupted to seal off fluid flow to the drainage bag. The valve apparatus includes a seal assembly that is configured to automatically move between the open position and the closed position in response to attaching an additional line or syringe to an auxiliary access port of the valve apparatus, thereby removing any potential for accidental release of fluids or misdirection of fluid flow.

Figure 1:
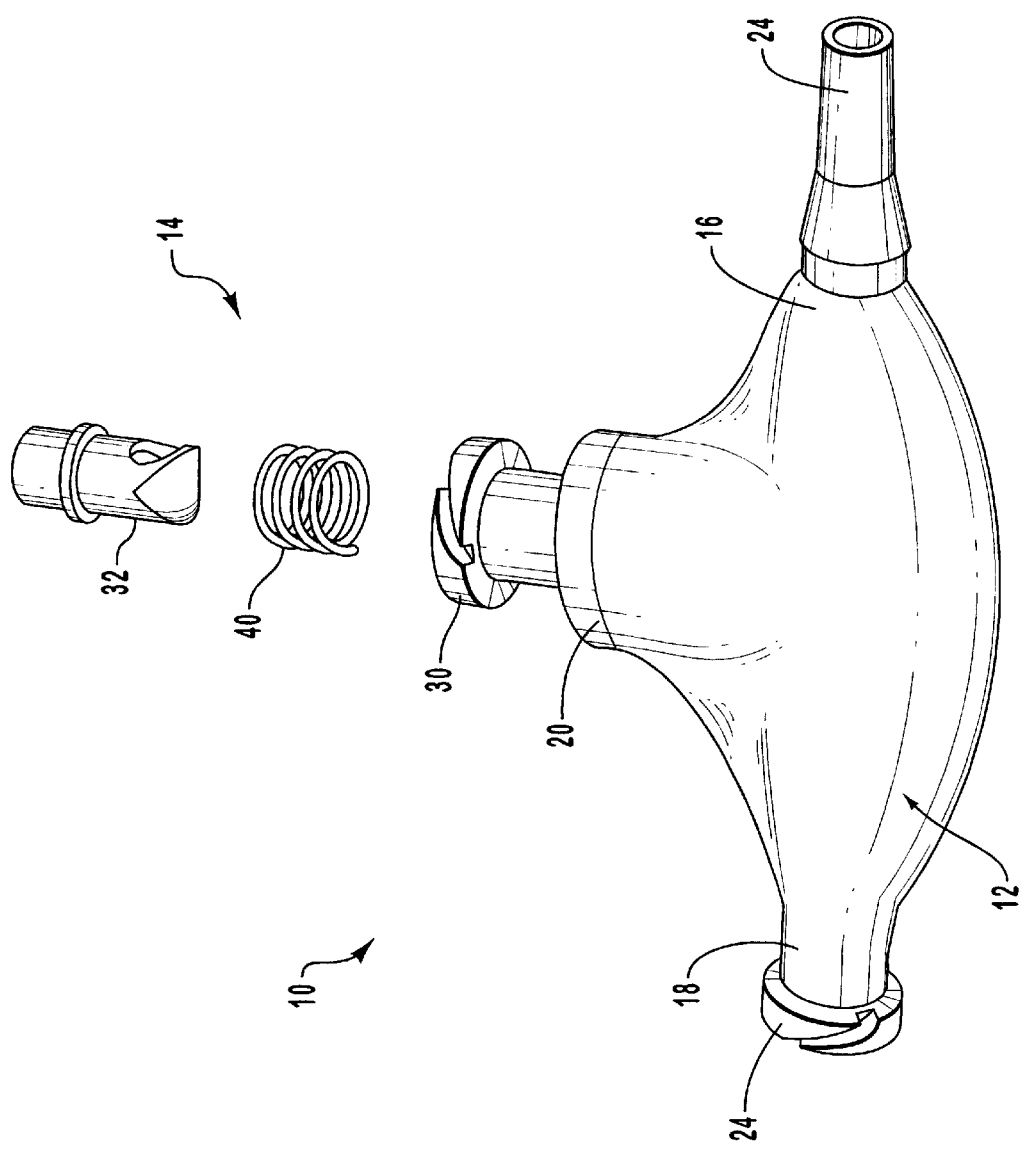
FIG. 1 is a partially exploded perspective view of one embodiment of a valve apparatus.
Figure 2:
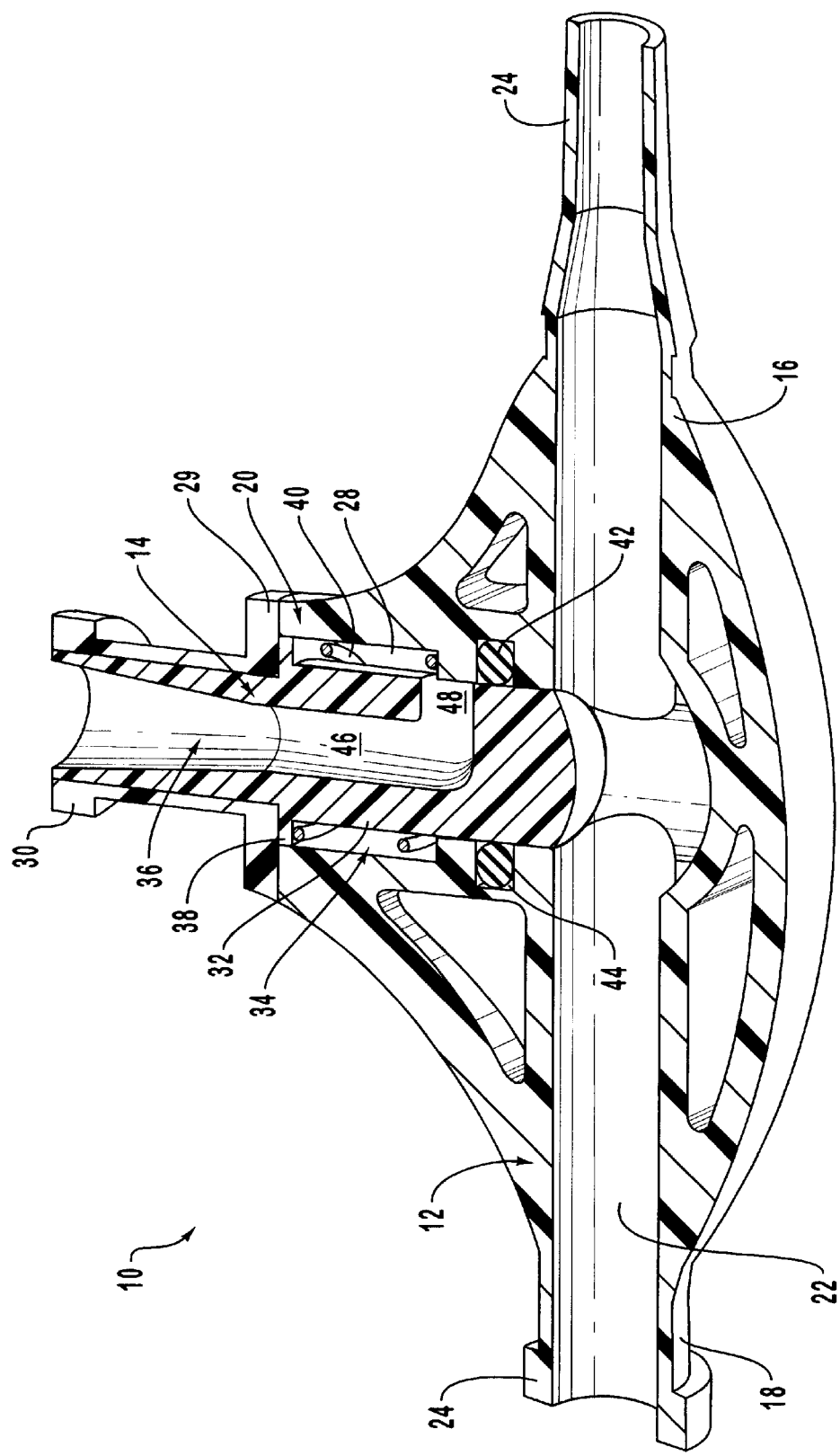
FIG. 2 is an enlarged cross-sectional view of the structure of FIG. 1 with the seal assembly in the open position.

FIG. 1 depicts one embodiment of a valve apparatus, such as valve apparatus 10. As illustrated, valve apparatus 10 comprises ahousing 12 andaseal assembly 14. Housing 12 has a proximal end 16, a distal end 18, and an access port 20. As shown in FIG. 2, housing 12 has a passageway 22 that extends longitudinally therethrough. In one embodiment, passageway 22 is sized and configured to eliminate the typical bottleneckingeffect on fluid flow that is found in conventional stopcocks. As a result, the diameter of passageway 22 is larger than the diameter of a passageway found in a conventional stopcock. Various sizes and configurations of passageway 22, however, may be utilized in housing 12. Although the interior surface of passageway 22 is shown in FIG. 2 as being substantially smooth, it will be appreciated by one skilled in the art that in an alternate embodiment passageway 22 can be grooved.

As illustrated in FIGS. 1 and 2, proximal end 16 and distal end 18 of housing 12 each have a connector 24 attached thereto. While various types of connectors 24 may be utilized, FIGS. 1 and 2 depict connector 24 that is attached to proximal end 16 of housing 12 as being, by way of example and not limitation, a male Luer lock hub to allow connection with standard tubes and catheters. Correspondingly, distal end 18 of housing 12 may be equipped with connector 24 that in this case is in the form of a female Luer lock hub to allow housing 12 to be connected to various types of medical devices including tubes, catheters, and a drainage bag (not shown). It will be appreciated that the position of the male and female Luer lock hubs could be reversed or that both connectors 24 could be the same configuration without affecting the function thereof. Another type of connector that may be used is a pressure-fit connector. It will be appreciated that a combination of different types of connectors may also be used.

Housing 12 also includes access port 20. Access port 20 is used for maintenance procedures for the tube or catheter, such as a flushing process where fluids are introduced into the tube or catheter to remove any particulates or other materials which may build up n the interior surface of the lumen thereof. As illustrated in FIG. 2, access port 20 has a bore (not shown) formed therethrough that is selectively in fluid communication with passageway 22 of housing 12. The bore formed through access port 20 is substantially concentric to access port 20. It will be appreciated that this is not required. In addition, as shown in FIG. 2, the bore of access port 20 has a recessed chamber 28 formed therein that communicates with the bore formed in access port 20. In one embodiment, chamber 28 is concentric with the bore in access port 20. It can be appreciated that housing 12 may have various other configurations in order to carry out the intended finction thereof.

The remote end of access port 20 is configured to be placed in fluid communication with a medical device. As depicted in FIGS. 1 and 2, the remote end of access port 20 includes a cap 29 with a connector 30 attached thereto for fluid coupling between a medical device (not shown) and access port 20. Cap 29 covers the remote end ofaccess port 20. Cap 29 is attached to access port 20 of housing 12 using conventional attachment techniques including adhesives or welding. In one embodiment, connector 30 is a conventional female Luer lock hub. Like connectors 24, which were previously discussed, connector 30 could have various other configurations and be a different type of connector other than a Luer lock hub. In addition, connectors 24 and 30 may have threads formed thereon to accommodate a conventional Luer locks attachment. Various other types of attachment structure or connectors may perform the attaching function of connectors 24 and 30.

The exterior of housing 12 is depicted in FIG. 1 as being substantially smooth. It will be appreciated that, the exterior of house 12 could have other configurations without affecting the function thereof. Although housing 12 is depicted as having one access port 20, housing 12 could have more than one access port attached thereto. In addition, in FIG. 2, access port 20 of housing 12 is depicted as being at an angle to passageway 22 formed through housing 12. It is contemplated that access port 20 could be positioned at various other angles relative to the longitudinal axis of passageway 22 than that illustrated in the figures. The angle of access port 20 is not important as long as access port 20 is in communication with passageway 22 formed through housing 12. It is intended that various other configurations of access port 20 are capable of performing the finction thereof with equal effectiveness.

Figure 3:
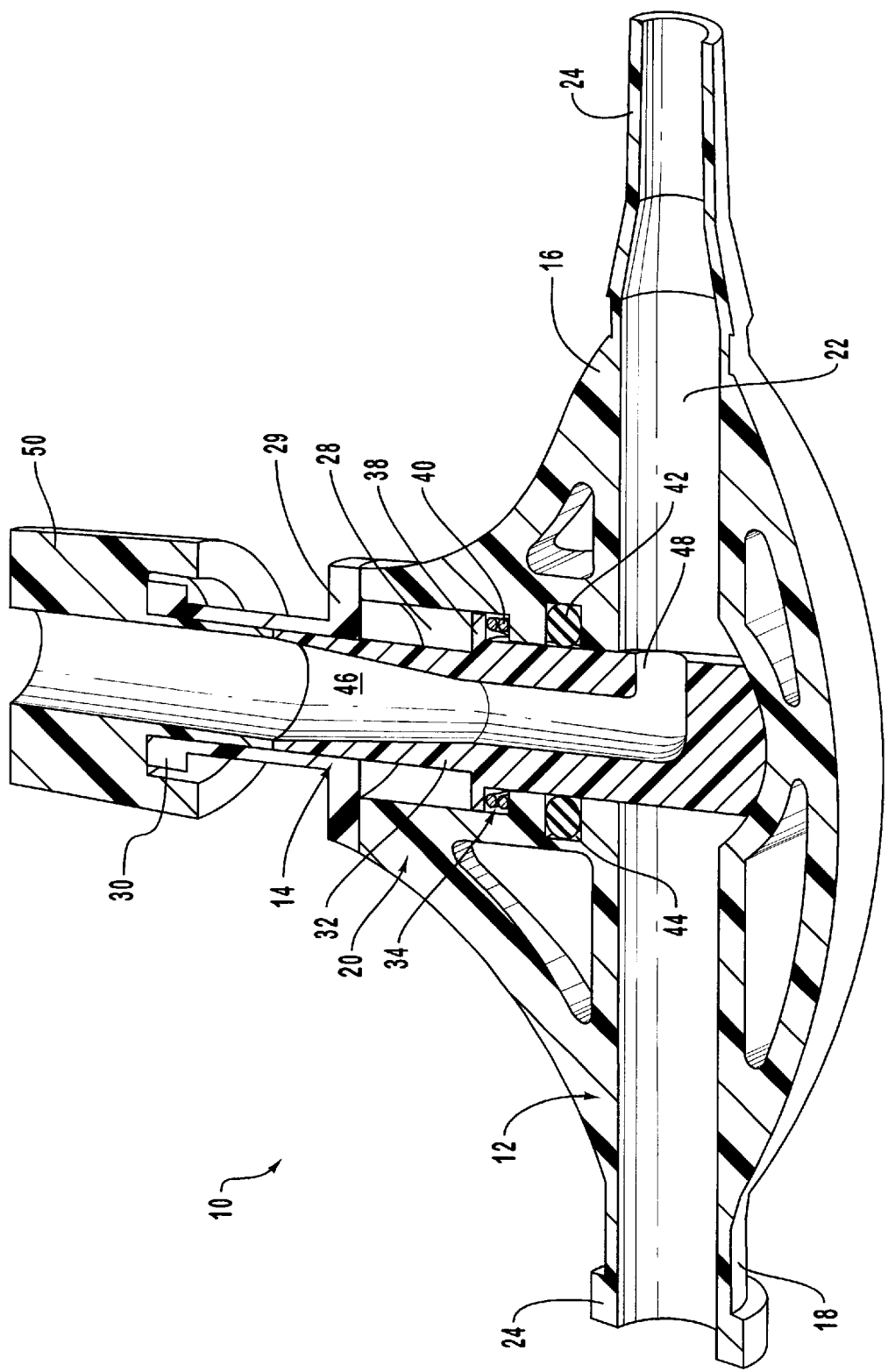
FIG. 3 is an enlarged cross-sectional view of the structure of FIG. 1 with the seal assembly in the closed position.

Valve apparatus 10 also includes seal assembly 14. Seal assembly 14 is configured to cooperate with the bore (not shown) formed in access port 20 and passageway 22. Seal assembly 14 automatically seals and unseals passageway 22 in housing 12 in response to a medical device being attached to connector 30 on the remote end of access port 20. Seal assembly 14 has an open position in which passageway 22 of housing 12 is capable of having fluid flow therethrough (FIG. 2) and a closed position in which the fluid flow through passageway 22 is interrupted and passageway 22 is sealed to prevent fluid from flowing out passageway 22 (FIG. 3). Seal assembly 14 automatically moves between the open position and the closed position in response to a medical device being mounted on connector 30 of access port 20. Seal assembly 14 is biased into the normally open position illustrated in FIG. 2.

Referring to FIG. 2, seal assembly 14 comprises a seal 32 and a biasing mechanism 34. Seal 32 is configured to cooperate with the bore and chamber 28 formed in access port 20 of housing 12 and is movably disposed in access port 20 for reciprocal motion between the open and closed positions, as indicated collectively in FIGS. 1 and 3. Seal 32 has a hole 36 formed therethrough. The exterior surface of seal 32 is configured to cooperate with the inner surface of the bore in access port 20. In one embodiment, seal 32 has a generally cylindrical shape and comprises a collar 38 that extends substantially outward from the exterior surface of seal 32. Collar 38 of seal 32 has an outer diameter approximately equal to the diameter formed by the inner surface of chamber 28. It can be appreciated that seal 32 may have other configurations as long as seal 32, the bore of access port 20, and chamber 32 are configured to cooperate and to allow seal 32 to be movably disposed in the bore of access port 20. The end of seal 32 proximate to passageway 22 is configured to sealingly engage the interior surface of passageway 22 when seal assembly 14 is in the closed position depicted in FIG. 3.

As previously discussed, seal 32 is biased into the normally open position depicted in FIG. 2. Seal 32 is configured to automatically move between the open and closed position thereby sealing and unsealing passageway 22 in response to a medical device being attached to access port 20. Seal 32 has a normally open position depicted in FIG. 2 in which passageway 22 is open and a closed position shown in FIG. 3 in which passageway 22 is sealed. Seal 32 may be composed of a resilient material such as a rubber or various other polymer materials.

Seal assembly 14 also comprises biasing mechanism 34 that is configured to urge seal 32 into the normally open position. In one embodiment, biasing mechanism 34 comprises a resilient flexible member 40, such as a spring, and collar 38 attached to seal 32. Spring 40 and collar 38 are disposed in chamber 28 of access port 20. Spring 40 is sized and configured so as to cooperate with collar 38 of seal 32 while being disposed in chamber 28. Spring 40 urges collar 38 and, consequently, seal 32 toward the remote end of access port 20. As a result, biasing mechanism 34 urges seal 32 into the normally open position. Resilient flexible member 40 may have various other configurations known by those skilled in the art such as a leaf spring or a resilient polymer seal.

In addition, it will be appreciated that biasing mechanism 34 may be located in various other positions and perform the function thereof. By way of example, instead of being disposed in chamber 28 of access port 20, biasing mechanism 34 could be attached to the exterior of access port 20. In that case connector 30 would be a male Luer lock assembly. Biasing mechanism would be attached to seal 32 through openings or slots formed in the wall of access port 20. Alternatively, collar 38 of seal 32 would extend outside of access port 20. In these embodiments, biasing mechanism 34 would comprise a resilient material that allows seal to move between a closed position and an open position but urges seal assembly 14 to return to the open position.

Biasing mechanism 34 is one embodiment of structure capable of performing the function of a biasing means for urging seal 32 into the open position. It can be appreciated various other embodiments of structure are capable of performing the function of such a biasing means for urging seal 32 into a normally open position. In addition, other structures capable of performing the function of a biasing means include, by way of example and not limitation, various other resilient members positioned within the bore of access port 20 to create resistance against seal 32.

Valve apparatus 10 also comprises a secondary seal 42. In one embodiment, secondary seal 42 is an O-ring that is disposed in an annular groove 44 formed in the bore of access port 20 proximate to passageway 22. Secondary seal 42 prevents any fluid liquid from seeping around the exterior surface of seal 32. Other embodiments of secondary seal 42 to prevent fluid seepage around the exterior surface of seal 32 are known by those skilled in the art. Further, instead of having secondary seal 42 distinct from seal 32, secondary seal 42 could be attached to seal 32 toward the end thereof proximate to passageway 22. This would eliminate the need for annular groove 44 as long as chamber 28 was configured to cooperate with the outside diameter of secondary seal 42.

FIG. 3 depicts seal 32 in the closed position upon a medical device 50 being attached to connector 30 of access port 20. Attaching medical device 50 to connector 30 causes the connector on medical device 50 to act on seal assembly 14 as will be discussed below in further detail. When seal 32 is in the closed position, hole 36 in seal 32 communicates with the bore in access port 20 and provides an opening to passageway 22. Upon seal 32 moving to the closed position, fluid having a slight pressure can be directed into hole 36 and enters passageway 22 thereby flushing the tube or catheter and cleaning out any particulates or blockages which may have formed therein. As soon as the cleansing fluid has been directed into the tube or catheter, medical device 50, such as a syringe, is unhooked from connector 30 on access port 20, and seal 32 automatically returns to the open position illustrated in FIG. 2 due to biasing mechanism 34 urging seal 32 toward the remote end of access port 20. As a result, passageway 22 goes from being in the closed position, as shown in FIG. 3, to being in the normally open position shown in FIG. 2.

As illustrated in FIGS. 2 and 3, in one embodiment hole 36 formed through seal 32 has a first portion 46 and a second portion 48. First portion 46 of hole 36 is substantially parallel to the longitudinal axis of seal 32. In contrast, second portion 48 of hole 36 is substantially parallel to the longitudinal axis of passageway 22 of housing 12. As depicted, first portion 46 and second portion 48 of hole 36 are substantially perpendicular thereby forming a right angled turn. It can be appreciated by those skilled in the art that hole 36 of seal 32 may have various other configurations. For example, first portion 46 and second portion 48 of hole 36 could have a more gradual curvature. The specific configuration of hole 36 is not particularly important as long as fluid that is directed through access port 20 enters hole 36 of seal 32 in access port 20 and exits seal 32 into passageway 22 of housing 12 so that the tube or catheter can be flushed. By way of example and not limitation, it can be appreciated that seal assembly 14 is one embodiment of structure capable of performing the function of sealing means for selectively sealing and unsealing passageway 22 of housing 12.

The inventive design of valve assembly 10 provides sterile access to, for example, a drainage catheter previously placed in the patient to remove obstructed bile, urine, or pus. Valve apparatus 10 allows a physician, patient, or nurse to use a standard Luer lock syringe to sterilely flush the catheter or tube. Further, unlike existing flush systems, valve apparatus 10 removes any possibility that a person flushing the catheter or tube will accidentally leave valve apparatus 10 in the closed position causing fluid to be misdirected. Rather than having medical personnel struggle to know which way the stopcock arm should be turned to direct flow, valve apparatus 10 with seal assembly 14 automatically moves between the open position and the closed position in response to a medical device 50, such as a syringe, being attached to access port 20.

One method of using valve apparatus 10 is by actuating seal assembly 14 using the manual compression caused by attaching a medical device 50 to the remote end of access port 20 as depicted in FIG. 3. The force exerted on seal assembly 14 by attaching syringe 50 to connector 30 on remote end of access port 20 overcomes the resistance force exerted on seal assembly 14 by biasing mechanism 34. Specifically, when syringe 50 is either Luer or friction locked into the remote end of access port 20, the forces acting on seal 32 by the connector of syringe 50 overcomes the biasing forces of spring 40 and automatically moves seal 32 to the closed position.

Once seal 32 has been moved to the closed position and passageway 22 is sealed, a one-way flush stream of cleansing fluid is directed into the tube or catheter from syringe 50 to clear the tube or catheter of any debris or build-up that might be in the lumen thereof. Upon syringe 50 being removed from connector 30 on access port 20, spring 40 urges seal 32 toward the remote end of access port 20. Consequently, seal 32 automatically moves back to the normally open position and allows the tube or catheter to drain by gravity. It can be appreciated that various other connectors and methods can be used to overcome the resistance of spring 40 to move seal 32 to the closed position.

Figure 4:
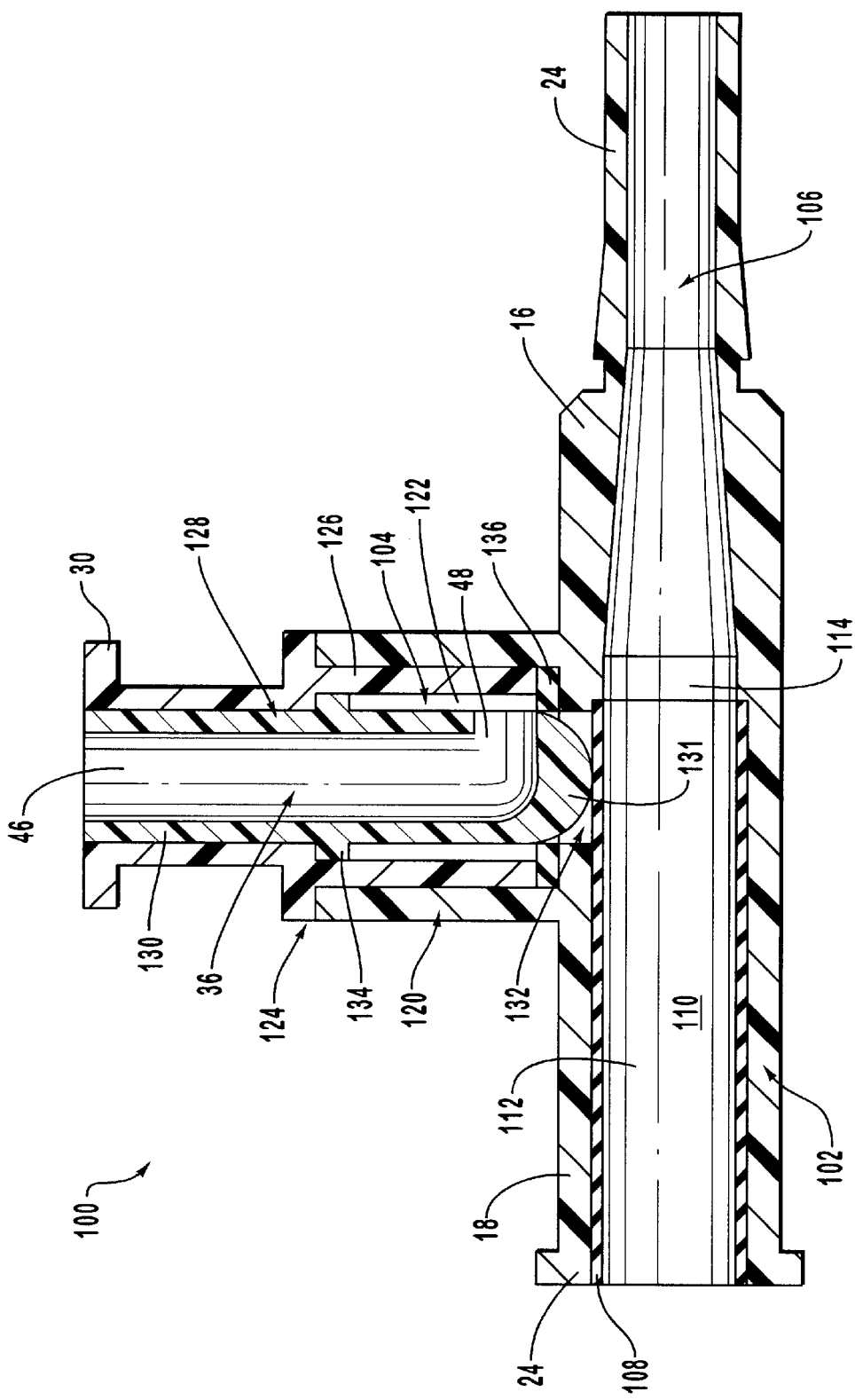
FIG. 4 is an enlarged cross-sectional view of another embodiment of a valve apparatus with a seal assembly in the open position.

FIGS. 4 and 5 illustrate a second embodiment of value apparatus 10, indicated generally as 100. The majority of the features previously discussed apply to valve apparatus 100. The features that are not affected are identified with the same reference numbers as used in FIGS. 1 through 3. Only those features that have changed will be described in detail.

As illustrated in FIG. 4, valve apparatus 100 comprises a housing 102 and seal assembly 104. Housing 102 has a passageway 106 that extends longitudinally therethrough. The interior surface of passageway 106 has been sized and configured to receive a resilient flexible member 108 therein. In one embodiment, resilient flexible member 108 comprises tubing.

Passageway 106 includes a first portion 112 and a second portion 114 proximate to resilient flexible member 108. The diameter of first portion 112 is larger than the diameter of second portion 114. As a result, the interior surface of passageway 106 has a step formed is therein to receive the end of resilient member 108. It can be appreciated that the interior surface of passageway 102 could have various other configurations as long as it is configured to cooperate with the end of resilient member 108. Resilient member 108 has a lumnen 110 formed therethrough with a diameter that is substantially the same as the diameter of second portion 114 of passageway 106. This allows passageway 106 and the inside surface of lumen 110 to form a substantially continuous and smooth surface.

Housing 102 also includes an access port 120 that has a bore (not shown) formed therethrough that is selectively in fluid conmmunication with passageway 106 of housing 102. In one embodiment of valve apparatus 100, access port 120 is substantially perpendicular to passageway 106 formed through housing 102. It will be appreciated that access port 120 could have various other orientations relative to passageway 106 in housing 102. As illustrated in FIG. 4, the bore of access port 120 also has a recessed chamber 122 formed therein that is concentric with the bore formed in access port 120. The bore formed through access port 120 is substantially concentric to access port 120. It will be appreciated that various other configurations and orientations of the bore through access port 120 could be used without affecting the function thereof.

Access port 120 includes a cap 124 attached to the remote end thereof. Cap 124 comprises a connector 30 that extends outwardly from access port 120 and a downwardly extending leg 126. The exterior surface of downwardly extending leg 126 is sized and configured to cooperate with the inside surface of chamber 122. Cap 124 is attached to access port 120 of housing 102 using conventional attachment techniques including, but not limited to, adhesives or welding.

Valve apparatus 100 also includes a seal assembly 128 that is depicted in FIG. 4. Seal assembly 128 is configured to cooperate with the bore (not shown) formed in access port 120 and to automatically seal and unseal passageway 106 in housing 102 in response to a medical device 50 being attached to connector 30. Seal assembly 128 has an open position in which the passageway of housing 102 is capable of having fluid flow therethrough (FIG. 4) and a closed position in which the fluid flow through passageway 106 is interrupted and passageway 106 is sealed to prevent fluid flow from flowing to the drainage bag (FIG. 5). Seal assembly 128 is biased into a normally open position illustrated in FIG. 4 as will be discussed in further detail below.

Referring to FIG. 4, seal assembly 128 comprises a seal 130 and a biasing mechanism 132. Seal 130 is configured to cooperate with bore and chamber 122 formed in access port 120 of housing 102 and is movably disposed in access port 120. Like seal 32 shown in FIGS. 2 and 3, seal 130 has a hole 36 formed therethrough and is configured to cooperate with the inner surface of the bore in access port 120.

In one embodiment, seal 130 includes an optional collar 134 that extends outward from the exterior surface of seal 130. Collar 134 of seal 130 has an outer diameter approximately equal to the diameter of formed by the inside diameter of leg 120. It can be appreciated that seal 130 may have other configurations as long as seal 130, the bore and chamber 122 of access port 120, and leg 120 of cap 124 are configured to cooperate so that seal 130 is movably disposed in the bore of access port 120. For example, if collar 134 was eliminated, the outside surface of seal 130 would contact the inside diameter of leg 120 of cap 124.

As previously discussed, seal 130 is biased into the normally open position depicted in FIG. 4. Seal 130 is automatically configured to move between the open and closed position thereby sealing and unsealing passageway 106 in response to medical device 50 being attached to access port 120. Seal 130 has the normally open position depicted in FIG. 4 in which passageway 106 is open and a closed position shown in FIG. 5 in which the passageway is sealed.

Seal assembly 128 also comprises a biasing mechanism 132 that is configured to urge seal 130 into the normally open position. In one embodiment, biasing mechanism 132 comprises resilient flexible member 108 and proximate end 131 of seal 130. It can be appreciated that various other types of biasing mechanisms 132 can be used to perform the finction thereof as will be discussed in further detail. Proximate end 131 of seal 130 is configured to engage the exterior surface of resilient flexible member 108 disposed in passageway 106 of housing 102 when seal assembly is in the closed position depicted in FIG. 5. As previously discussed, in one embodiment, resilient flexible member 108, illustrated in FIG. 4, comprises tubing disposed in passageway 106. When seal assembly 128 moves to the closed position depicted in FIG. 5, proximate end 131 of seal 130 engages the outside diameter of tubing 108 causing the end of tubing 108 to pinch down on itself, thereby sealing lumen 110 in tubing 108 and, as a result, passageway 106 though housing 102. Tubing 108 can be comprised of various resilient materials including rubber, silicon, or other resilient polymer materials. Tubing 108 must, however, be sufficiently flexible to form a seal when seal 130 is in the closed position and resilient enough to exert biasing forces on seal assembly 128.

When medical device 50 is removed from connector 30 on an access port 120, tubing 108 exerts a biasing force on proximate end 131 of seal 130 sufficient to urge seal 130 toward connector 30 and to return seal 130 to the normally open position. It will be appreciated that resilient flexible member or tubing 108 may have other configurations known by those skilled in the art. Tubing 108 is one embodiment of structure capable of performing the function of a biasing means for urging seal 130 into the open position. It can be appreciated that various other embodiments of structure are capable of performing the function of such a biasing means for urging seal into a normally open position. Other structures capable of performing the function of a biasing means include, by way of example and not limitation, various other resilient members positioned within passageway 106 of housing 102 capable of forming a seal against itself when seal 130 is in the closed position and resilient enough to urge seal 130 toward connector 30 and to return to the open position.

Valve apparatus 100 also comprises a secondary seal 136. In one embodiment, secondary seal 136 comprises a washer that is disposed in chamber 122 of access port 120. Other embodiments of secondary seal 136 to prevent fluid seepage around the exterior surface of seal are known by those skilled in the art. In addition, although secondary seal 136 is illustrated as being positioned in access port 120 near proximate end 131 of seal 130, it will be appreciated that secondary seal 136 may have various other positions within seal assembly 128. In addition, secondary seal 136 may have various other shapes and configurations than that depicted in FIGS. 4 and 5. By way of example and not limitation, secondary seal 136 may be attached to seal 132. The specific location of secondary seal is not particularly important. What is important, is that secondary seal 136 prevents fluid leakage from passageway 106 in housing 102.

The ability for valve apparatus 10 and 100 to automatically move between an open and a closed position provides a solution for several drainage complications. Seal assemblies 14 and 128 automatically move between sealing and unsealing passageway 22 and 106 within housing 12 and 102, respectively, without having to disconnect the catheter tubing or worry about directing flow by manually switching a valve on a conventional stopcock. Valve apparatus 10 and 100 are a no-nonsense, user-friendly, automatic device that will not restrict the fluid flow of tube or catheter.

It is envisioned that valve apparatus 10 and 100 will be used in a variety of applications involving tubes or catheters. In particular, one application is using valve apparatus 10 or 100 following the percutaneous or surgical placement of drainage catheters or tubes into obstructed organs, such as the urinary tract, or the biliary track to allow drainage of potentially infective body fluids such as urine or bile. Valve apparatus 10 or 100 may also be used with catheters or tubes that have been placed into abscess cavities. Valve apparatus 10 or 100 will be inserted within the drainage system between the catheter which has been placed within a body cavity and a drainage receptacle such as an enclosed drainage bag. Typically valve apparatus 10 or 100 will be actuated by flushing the system three to four times daily to prevent the accumulation of debris in the drainage catheter. It is contemplated that valve apparatus 10 or 100 may have utility for angiography applications or other applications within the cardiovascular or intravenous system. It is further envisioned that more than one valve apparatus 10 or 100 may be used in a series.

The present invention may be embodied in other specific forms without departing from its spirit or essential characteristics. The described embodiments are to be considered in all respects only as illustrative and not restrictive. The scope of the invention is, therefore, indicated by the appended rather than by the foregoing description. All changes which come within the meaning and range of equivalency of the claims are to be embraced within their scope.

What is claimed and desired to be secured by United States Letters Patent is:

1. A valve apparatus comprising:
   (a) a housing having a passageway formed therethrough, said housing further comprising an access port having a bore formed therein;
   (b) a seal assembly configured to automatically seal said passageway in said housing in response to attachment of a medical device to said access port and automatically unseal said passageway in response to detachment of said medical device from said access port, said seal assembly having an open position in which fluid is permitted to flow through said passageway of said housing and a closed position wherein said passageway is substantially sealed so that fluid flow therethrough is substantially interrupted, said seal assembly comprising:
   (i) a seal movably disposed in said bore of said access port; and
   (ii) a biasing mechanism including a collar attached to an outside surface of said seal and extending outwardly therefrom and said biasing mechanism including a resilient flexible member, said resilient flexible member cooperating with said collar to urge said seal into said open position.

2. A valve apparatus for facilitating flushing of a drainage tube used in a medical application, the valve apparatus comprising:

(a) a housing having a passageway formed therethrough and said passageway having proximal and distal ends, said housing further comprising an access port having a bore formed therein configured to facilitate selective establishment of a flow path between a first medical device and said passageway;

(b) tubing disposed inside at least a portion of said passageway; and (c) a seal slidingly disposed in said bore and having an open position wherein fluid is substantially free to flow between said proximal and distal ends of said passageway, and a closed position wherein fluid flow between said proximal and distal ends of said passageway is substantially prevented, said seal assuming said closed position in response to attachment of said first medical device to said access port and said seal assuming said open position in response to detachment of said first medical device from said access port, wherein in said closed position said seal pinches said tubing substantially shut so as to substantially prevent fluid flow between said proximal and distal ends of said passageway.

3. A valve apparatus comprising, (a) a housing having a passageway formed therethrough, said housing further comprising an access port having a bore formed therein configured so as to facilitate selective fluid communication between said access port and said passageway;

(b) a seal assembly having an open position in which fluid is permitted to flow through said passageway of said housing and a closed position wherein said passageway is sealed so that fluid flow therethrough is interrupted, said seal assembly being configured to automatically seal said passageway in said housing in response to attachment of a medical device to said access port and automatically unseal said passageway in response to removal of said medical device from said access port, said seal assembly being biased into said open position, said seal assembly having a flushing passage formed therethrough which communicates with said bore in said access port and provides an opening to said passageway of said housing when said seal assembly is in said closed position, and said seal assembly comprising:

(i) a seal sized and configured to cooperate with said bore of said access port, said seal being movably disposed in said bore of said access port; and (ii) a biasing mechanism including a collar attached to an outside surface of said seal and extending substantially outward therefrom and said biasing mechanism including a resilient flexible member, said resilient flexible member cooperating with said collar to urge said seal into said open position.

4. A valve apparatus as recited in claim 3, further comprising a chamber formed in said bore in said access port, said chamber being sized and configured to receive said collar of said seal and said resilient flexible member therein.

5. The valve apparatus as recited in claim 2, wherein said proximal end of said passageway is in fluid communication with a second medical device and said distal end of said passageway is in fluid communication with the drainage tube, so that when said seal is in said open position, fluid is substantially free to flow between said second medical device and the drainage tube and when said seal is in said closed position, fluid flow between said second medical device and the drainage tube is substantially prevented.

6. The valve apparatus as recited in claim 5, wherein said second medical device comprises a catheter.

7. The valve apparatus as recited in claim 2, wherein said tubing is substantially composed of a resilient material which serves to bias said seal toward said open position so that upon detachment of said first medical device from said access port, said seal moves automatically into said open position.

8. The valve apparatus as recited in claim 7, wherein said tubing is substantially composed of materials selected from the group consisting of rubbers, polymers, and silicon.

9. The valve apparatus as recited in claim 2, wherein movement of said seal to said closed position facilitates establishment of a flow path between said first medical device and said proximal end of said passageway and wherein a second medical device is in fluid communication with said proximal end of said passageway so that flushing material introduced by said first medical device passes through said proximal end of said passageway and into said second medical device.

10. The valve apparatus as recited in claim 2, wherein said seal defines a flushing passage therethrough in fluid communication with said access port, fluid flow between said flushing passage and said proximal end of said passageway being substantially prevented when said seal is in said open position, and said flushing passage moving into alignment with said proximal end of said passageway so as to facilitate establishment of a flow path between said first medical device and said proximal end of said passageway when said seal moves to said closed position.

11. A drainage system for use in medical applications, the drainage system comprising:

(a) a valve apparatus including:

(i) a housing having a passageway formed therethrough and the passageway having proximal and distal ends, said housing further comprising an access port having a bore formed therein;

(ii) tubing disposed inside at least a portion of said passageway; and (iii) a seal slidingly disposed in said bore and having at least an open position wherein fluid is substantially free to flow between said proximal and distal ends of said passageway and a closed position wherein fluid flow between said proximal and distal ends of said passageway is substantially prevented, said seal assuming said closed position in response to attachment of a first medical device to said access port and said seal assuming said open position in response to detachment of said first medical device from said access port, wherein in said closed position said seal pinches said tubing substantially shut so as to substantially prevent fluid flow between said proximal and distal ends of said passageway;

(b) a catheter in fluid communication with said proximal end of said passageway;

(c) a drainage tube in fluid communication with said distal end of said passageway; and (d) a drainage reservoir in fluid communication with said drainage tube.

12. (New) The drainage system as recited in claim 11 wherein movement of said seal to said closed position facilitates establishment of a flow path between said first medical device and said proximal end of said passageway and wherein a second medical device is in fluid communication with said proximal end of said passageway so that flushing material introduced by said first medical device passes through said proximal end of said passageway and into said second medical device.

13. The drainage system as recited in claim 11 wherein said tubing biases said seal toward said open position so that said seal moves automatically into said open position upon detachment of said medical device from said access port.

14. A backflush valve for use in medical applications, comprising:
(a) a housing having a passageway formed therethrough, the passageway having distal and proximal ends, and said housing having an access port defining a bore;
(b) a seal defining a flushing passage therethrough configured for selective fluid communication with said passageway, and said seal being slidingly disposed in said bore of said access port for reciprocal motion between an open position and a closed position; and
(c) a biasing mechanism including:
(i) a collar disposed about said seal; and
(ii) a spring, said spring acting upon said collar so as to urge said seal toward a predetermined position.

15. A backflush valve for use in medical applications, comprising:
(a) a housing having a passageway formed therethrough, the passageway having distal and proximal ends, and said housing having an access port defining a bore;
(b) a seal defining a flushing passage therethrough configured for selective fluid communication with said passageway, said seal being slidingly disposed in said bore of said access port for reciprocal motion between an open position wherein said seal permits fluid to flow substantially freely between said distal and proximal ends of said passageway, and a closed position, said seal sliding into said open position in response to detachment of a medical device from said access port and said seal sliding into said closed position in response to attachment of said medical device to said access port; and
(c) tubing disposed in at least a portion of said passageway and biasing said seal into said open position, and said tubing being pinched substantially shut by said seal so that flow between said distal and proximal ends of said passageway is substantially prevented when said seal is in said closed position.

16. A backflush valve for use in medical applications, comprising:
(a) a housing having a passageway formed therethrough, the passageway having distal and proximal ends, and said housing having an access port defining a bore;
(b) a seal defining a flushing passage therethrough having a first end and a second end, said seal being slidingly disposed in said bore of said access port so that upon attachment of a medical device to said access port said seal slides into a closed position wherein said first end of said flushing passage is substantially aligned with said medical device and said second end of said flushing passage is substantially aligned with said passageway so that a fluid path is established between said medical device and said proximal end of said passageway and wherein said seal enters said passageway so as to substantially prevent fluid flow between said distal and proximal ends of said passageway, and upon detachment of said medical device from said access port, said seal moves into an open position wherein said seal is substantially retracted from said passageway so that fluid is substantially free to flow between said distal and proximal ends of said passageway and wherein said second end of said flushing passage moves out of alignment with said proximal end of said passageway so that fluid communication between said flushing passage and said passageway is substantially prevented; and
(c) resilient tubing disposed inside at least a portion of said passageway, said resilient tubing biasing said seal toward said open position when said medical device has been detached from said access port, and said resilient tubing being substantially pinched shut by said seal when said seal in said closed position so that flow between said proximal and distal ends of said passageway is substantially prevented.

17. The valve apparatus as recited in claim 1, wherein said passageway comprises distal and proximal ends and said seal defines a flushing passage therethrough in fluid communication with said bore of said access port, fluid flow between said flushing passage and said proximal end of said passageway being substantially prevented when said seal is in said open position, and said flushing passage moving into alignment with said proximal end of said passageway so as to facilitate establishment of a flow path between said medical device and said proximal end of said passageway when said seal moves to said closed position.

18. The valve apparatus as recited in claim 1, further comprising a chamber formed in said bore in said access port, said chamber being sized and configured to receive said collar of said seal assembly and said resilient flexible member therein.

19. The valve apparatus as recited in claim 3, wherein when said seal is in said open position, fluid communication between said bore in said access port and said passageway is substantially prevented.

20. The backflush valve as recited in claim 14, wherein said flushing passage comprises first and second ends, said first end of said flushing passage being substantially aligned with said bore of said access port and said second end of said flushing passage being arranged for selective alignment with said passageway so that when said seal is in said closed position a flow path is established between said access port and said proximal end of said passageway, and when said seal is in said open position, flow between said access port and said proximal end of said passageway is substantially prevented.

21. The backflush valve as recited in claim 14, wherein in said closed position, said seal substantially prevents flow between said distal and proximal ends of said passageway.

22. The backflush valve as recited in claim 14, wherein in said open position, said seal is positioned to permit flow between said distal and proximal ends of said passageway.

23. The backflush valve as recited in claim 14, wherein said predetermined position of said seal comprises said open position.

24. The backflusb valve as recited in claim 15, wherein said tubing comprises a material selected from the group consisting of rubbers, polymers, and silicon.

25. The backflush valve as recited in claim 15, wherein an end of said flushing passage is substantially aligned with said bore of said access port so that when said seal is in said closed position a flow path is established between said access port and said proximal end of said passageway, and when said seal is in said open position, flow between said access port and said proximal end of said passageway is substantially prevented.

* * * * *